(12) United States Patent
Takei

(10) Patent No.: US 10,796,796 B2
(45) Date of Patent: Oct. 6, 2020

(54) FAULT DIAGNOSIS APPARATUS, FAULT DIAGNOSIS METHOD, AND FAULT DIAGNOSIS PROGRAM

(71) Applicant: FUJIFILM Corporation, Tokyo (JP)

(72) Inventor: Mizuki Takei, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 418 days.

(21) Appl. No.: 15/909,180

(22) Filed: Mar. 1, 2018

(65) Prior Publication Data

US 2018/0190378 A1 Jul. 5, 2018

Related U.S. Application Data

(63) Continuation of application No. PCT/JP2016/073625, filed on Aug. 10, 2016.

(30) Foreign Application Priority Data

Sep. 24, 2015 (JP) .................................. 2015-187381

(51) Int. Cl.
*G06F 11/30* (2006.01)
*G16H 40/40* (2018.01)
*G05B 23/02* (2006.01)

(52) U.S. Cl.
CPC ............. *G16H 40/40* (2018.01); *G05B 23/02* (2013.01); *G05B 23/0267* (2013.01); *G05B 2219/32287* (2013.01)

(58) Field of Classification Search
None
See application file for complete search history.

(56) References Cited

U.S. PATENT DOCUMENTS

| 9,933,338 B2 * | 4/2018 | Noda .................... G05B 23/024 |
| 2013/0132001 A1 * | 5/2013 | Yacout .................... G06N 20/00 |
| | | 702/35 |
| 2018/0150344 A1 * | 5/2018 | Kim .................... G06F 11/0709 |

FOREIGN PATENT DOCUMENTS

| JP | 2001-306131 A | 11/2001 |
| JP | 2009-021348 A | 1/2009 |

(Continued)

OTHER PUBLICATIONS

International Search Report issued in PCT/JP2016/073625; dated Oct. 4, 2016.

(Continued)

*Primary Examiner* — Aditya S Bhat
(74) *Attorney, Agent, or Firm* — Studebaker & Brackett PC

(57) ABSTRACT

A fault diagnosis apparatus acquires, by using an acquisition unit, for each of a plurality of medical devices, installation environment information including a plurality of items about an installation environment in which each of the plurality of medical devices is installed; classifies, by using a classification unit, the plurality of medical devices into a plurality of groups on the basis of the installation environment information; extracts, by using an extraction unit, an item in the installation environment information representing a feature of a group to which a device in which a fault has occurred among the plurality of medical devices belongs, the feature being different from that of the other groups; and performs control, by using a display control unit, to cause a display unit to display an extraction result obtained by the extraction unit.

20 Claims, 10 Drawing Sheets

(56) References Cited

FOREIGN PATENT DOCUMENTS

| JP | 5039739 B2 | 10/2012 |
|----|------------|---------|
| JP | 5530019 B1 | 6/2014  |

OTHER PUBLICATIONS

Written Opinion issued in PCT/JP2016/073625; dated Oct. 4, 2016.
International Preliminary Report on Patentability issued in PCT/JP2016/073625; dated Oct. 4, 2016.

* cited by examiner

| | INSTALLATION ENVIRONMENT INFORMATION | | | | | | |
|---|---|---|---|---|---|---|---|
| IDENTIFICATION NO. | HARDWARE INFORMATION | | SOFTWARE INFORMATION | | MAINTENANCE INFORMATION | | |
| SERIAL NO. | CONNECTED DEVICE | ... | MODULE A Ver. | ... | FAULT FREQUENCY | INSPECTION FREQUENCY | ... |
| 123 | (DEVICE C, DEVICE D, DEVICE Y, ...) | ... | V9.0.0010 | ... | 1 | 10 | ... |
| 456 | (DEVICE B, DEVICE V, DEVICE Z, ...) | ... | V7.3.0410 | ... | 5 | 4 | ... |
| 780 | (DEVICE E, DEVICE H, DEVICE S, ...) | ... | V8.4.9999 | ... | 0 | 20 | ... |
| ... | ... | ... | ... | ... | ... | ... | ... |

32A

DIAGNOSTIC RESULT DISPLAY SCREEN

The fault occurrence device belongs to a group having the feature of being connected to device X.

| IDENTIFICATION NO. | FAULT INFORMATION | | | |
|---|---|---|---|---|
| SERIAL NO. | FAULT IDENTIFICATION INFORMATION | TIME-AND-DATE INFORMATION | ... |
| 123 | A001 | 2014/11/22 8:53 | ... |
| 456 | B134 | 2013/4/4 19:36 | ... |
| 780 | F206 | 2011/9/16 14:22 | ... |
| ... | ... | ... | ... |

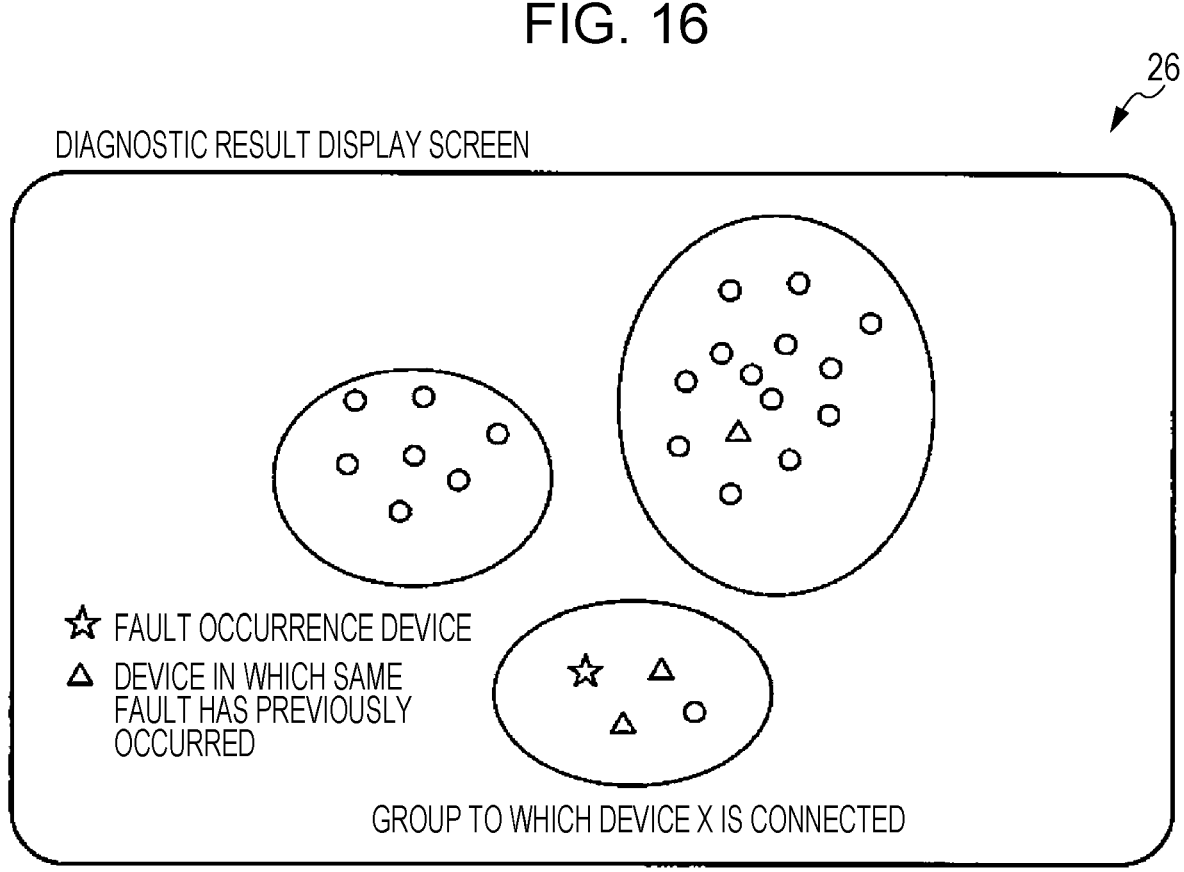

FAULT DIAGNOSIS APPARATUS, FAULT DIAGNOSIS METHOD, AND FAULT DIAGNOSIS PROGRAM

CROSS-REFERENCE TO RELATED APPLICATIONS

This application is a Continuation of PCT International Application No. PCT/JP2016/073625 filed on Aug. 10, 2016, which claims priority under 35 U.S.C § 119(a) to Japanese Patent Application No. 2015-187381 filed on Sep. 24, 2015. Each of the above application(s) is hereby expressly incorporated by reference, in its entirety, into the present application.

BACKGROUND OF THE INVENTION

1. Field of the Invention

The present invention relates to a fault diagnosis apparatus, a fault diagnosis method, and a non-transitory computer readable recording medium storing a fault diagnosis program.

2. Description of the Related Art

In the related art, there are known techniques related to location of causes of faults in devices such as electronic devices and techniques for detecting signs of the faults. As a technique of this type, JP5039739B discloses a fault position examination device that locates the position of a fault that has occurred in a network. In this fault position examination device, network devices are related with customer information and, in addition, fault information is associated with a combination of states of network devices. In this fault position examination device, furthermore, upon receipt of an inquiry from a customer regarding a fault, states of network devices related with the customer are collected. In this fault position examination device, furthermore, fault information associated with a combination of collected states of network devices is acquired, thus enabling examination of fault information about a specific customer without checking the entire network.

JP5530019B discloses a detection system for detecting a sign of an anomaly of machine equipment. In this detection system, time-series data including sensor data is acquired from the machine equipment as observation data and normal operation data that has been previously acquired is clustered. In this detection system, furthermore, a cluster having a minimum distance from the observation data is selected from among two or more clusters obtained as a result of clustering, and a sign of an anomaly of the machine equipment is detected on the basis of the magnitude of the distance between the selected cluster and the observation data.

SUMMARY OF THE INVENTION

In a case where a maintenance person handles a device in which a fault has occurred, it is preferable to notify the maintenance person of a possible cause of the fault to help the maintenance person perform an operation of identifying the cause of the fault.

In the technique disclosed in JP5039739B, however, fault information to be acquired is limited to known information. If a sufficient amount of fault information is not accumulated or if an unknown fault occurs, a possible cause of the fault is not extractable in many cases.

On the other hand, the technique disclosed in JP5530019B is used to detect a sign of a fault in a device and is not intended to extract a possible cause of the fault from a cluster obtained as a result of clustering.

The present invention has been made in view of the foregoing situation, and it is an object of the present invention to provide a fault diagnosis apparatus, a fault diagnosis method, and a non-transitory computer readable recording medium storing a fault diagnosis program that are capable of assisting an operation of identifying the cause of a fault in a device in which the fault has occurred.

To achieve the object described above, a fault diagnosis apparatus according to an aspect of the present invention includes an acquisition unit that acquires, for each of a plurality of devices, installation environment information including a plurality of items about an installation environment in which each of the plurality of devices is installed, a classification unit that classifies the plurality of devices into a plurality of groups on the basis of the installation environment information, an extraction unit that extracts an item in the installation environment information representing a feature of a group to which a device in which a fault has occurred among the plurality of devices belongs, the feature being different from a feature of other groups, and a display control unit that performs control to cause a display unit to display an extraction result obtained by the extraction unit.

In the fault diagnosis apparatus according to the aspect of the present invention, the classification unit may perform the classification on the basis of an item in the installation environment information, the item being a possible cause of occurrence of the fault.

In the fault diagnosis apparatus according to the aspect of the present invention, furthermore, the display control unit may perform control to cause the display unit to display a classification result obtained by the classification unit in an identifiable manner for each classified group.

In the fault diagnosis apparatus according to the aspect of the present invention, in particular, the display control unit may perform control to cause the display unit to display the classification result in such a manner as to enable the device in which the fault has occurred to be identified.

The fault diagnosis apparatus according to the aspect of the present invention may also include an accumulation unit that accumulates fault occurrence information in which fault information concerning a type of fault that has occurred in the device and identification information assigned to each of the plurality of devices are associated with each other. The acquisition unit may acquire the fault information of the device in which the fault has occurred, and the display control unit may perform control to cause the display unit to display the plurality of groups in such a manner that, on the basis of the fault occurrence information accumulated by the accumulation unit, a device in which the same type of fault as a type of fault indicated by the fault information acquired by the acquisition unit has occurred is recognizable.

In the fault diagnosis apparatus according to the aspect of the present invention, furthermore, the installation environment information may include a plurality of items about at least one of information concerning hardware of a device to which the device is connected, information concerning software used in the device, or information concerning maintenance of the device.

In the fault diagnosis apparatus according to the aspect of the present invention, furthermore, the extraction unit may extract items in the installation environment information, each item representing one of a plurality of features as the different feature in descending order from a feature having a highest degree of difference.

The fault diagnosis apparatus according to the aspect of the present invention may further include an acceptance unit that accepts an input of the installation environment information of the device in which the fault has occurred. The classification unit may classify, on the basis of the installation environment information accepted by the acceptance unit, the device in which the fault has occurred in any one of a plurality of groups classified on the basis of the installation environment information acquired by the acquisition unit.

In the fault diagnosis apparatus according to the aspect of the present invention, the device may be a medical device.

To achieve the object described above, on the other hand, a fault diagnosis method according to another aspect of the present invention includes acquiring, for each of a plurality of devices, installation environment information including a plurality of items about an installation environment in which each of the plurality of devices is installed, classifying the plurality of devices into a plurality of groups on the basis of the installation environment information, extracting an item in the installation environment information representing a feature of a group to which a device in which a fault has occurred among the plurality of devices belongs, the feature being different from a feature of other groups, and performing control to cause a display unit to display an extraction result.

To achieve the object described above, furthermore, a non-transitory computer readable recording medium storing a fault diagnosis program according to still another aspect of the present invention causes a computer to function as an acquisition unit, a classification unit, an extraction unit, and a display control unit of the fault diagnosis apparatus according to the aspect of the present invention.

According to some aspects of the present invention, it is possible to assist an operation of identifying the cause of a fault in a device in which the fault has occurred.

BRIEF DESCRIPTION OF THE DRAWINGS

FIG. 16 is a schematic diagram illustrating an example of a diagnostic result display screen according to the third embodiment.

DESCRIPTION OF THE PREFERRED EMBODIMENTS

Exemplary embodiments for carrying out the present invention will be described in detail hereinafter with reference to the drawings. Here, a description will be given of exemplary embodiments in which a medical device is used as an electronic device to be diagnosed for a fault.

First Embodiment

Figure 1:
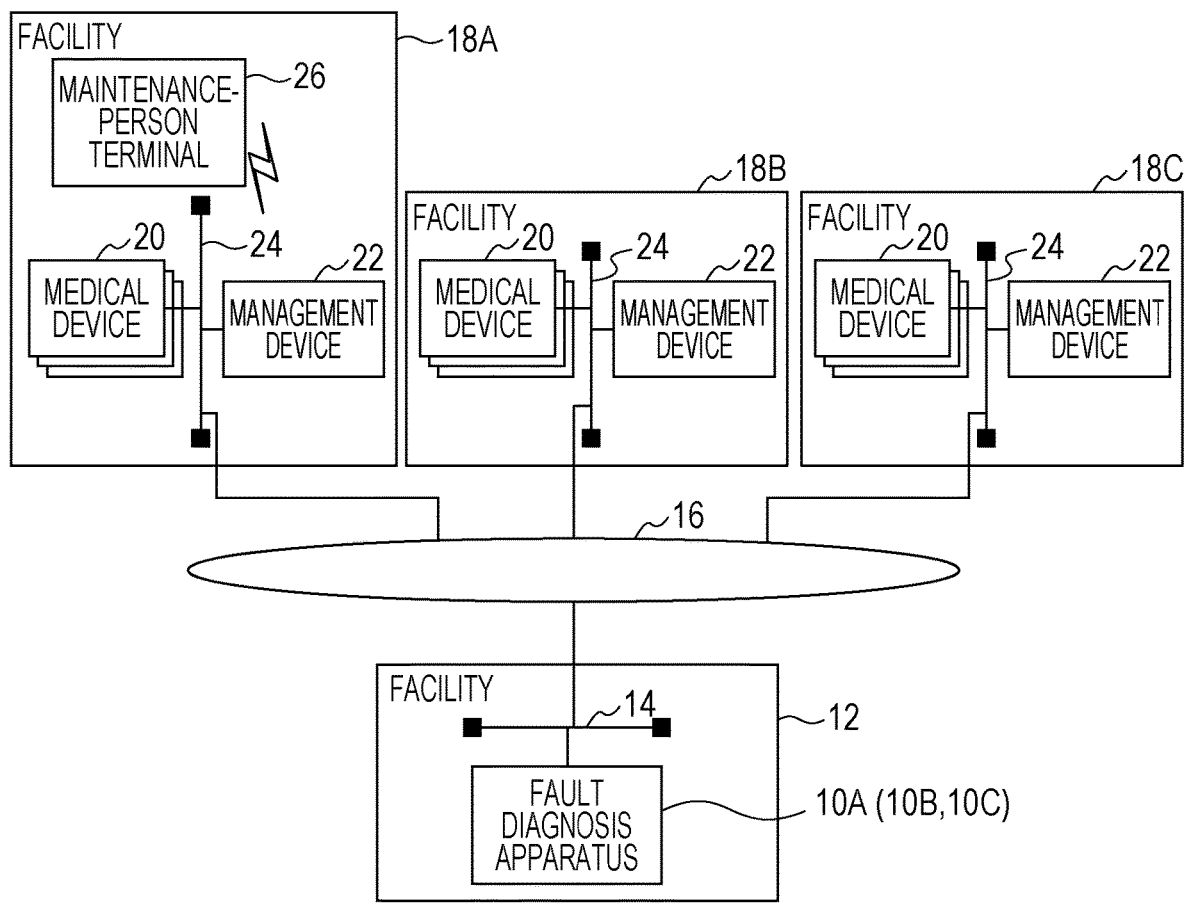
FIG. 1 is a block diagram illustrating an example of a connection configuration of a fault diagnosis apparatus, medical devices, and management devices according to embodiments.

First, a connection configuration of a fault diagnosis apparatus 10A, medical devices 20, and management devices 22 according to this embodiment will be described with reference to FIG. 1. As illustrated in FIG. 1, the fault diagnosis apparatus 10A according to this embodiment is placed in a facility 12 and is connected to a network 16 such as a WAN (Wide Area Network) via a network 14 such as a LAN (Local Area Network).

Further, in each of facilities 18A to 18C, a plurality of medical devices 20 to be diagnosed by the fault diagnosis apparatus 10A and a management device 22 that manages the medical devices 20 are installed. The medical devices 20 and the management device 22 are connected to each other via a network 24 such as a LAN, and the network 24 is connected to the network 16. Thus, the medical devices 20 in the facilities 18A to 18C and the fault diagnosis apparatus 10A in the facility 12 are capable of communicating with each other via the network 16.

In the following, when the facilities 18A to 18C are referred to collectively without being distinguished, the facilities 18A to 18C will be described with omission of the alphabetic letters that follow the numerals assigned thereto. In each facility 18, the medical devices 20 include devices that are electrically connected directly to each other without the intervention of the network 24 in accordance with the design specification, usage, or the like of the device. In FIG. 1, a state in which a mobile terminal 26 (hereinafter referred to as the "maintenance-person terminal 26") that is used by a maintenance person who performs maintenance on the medical devices 20 is brought into the facility 18A by the maintenance person is illustrated as an example. The maintenance-person terminal 26 is provided with a display device such as a display, and an input device such as a keyboard. Further, the maintenance-person terminal 26 is capable of communicating with any other device via the network 24 and the network 16 over wireless communication.

Figure 2:
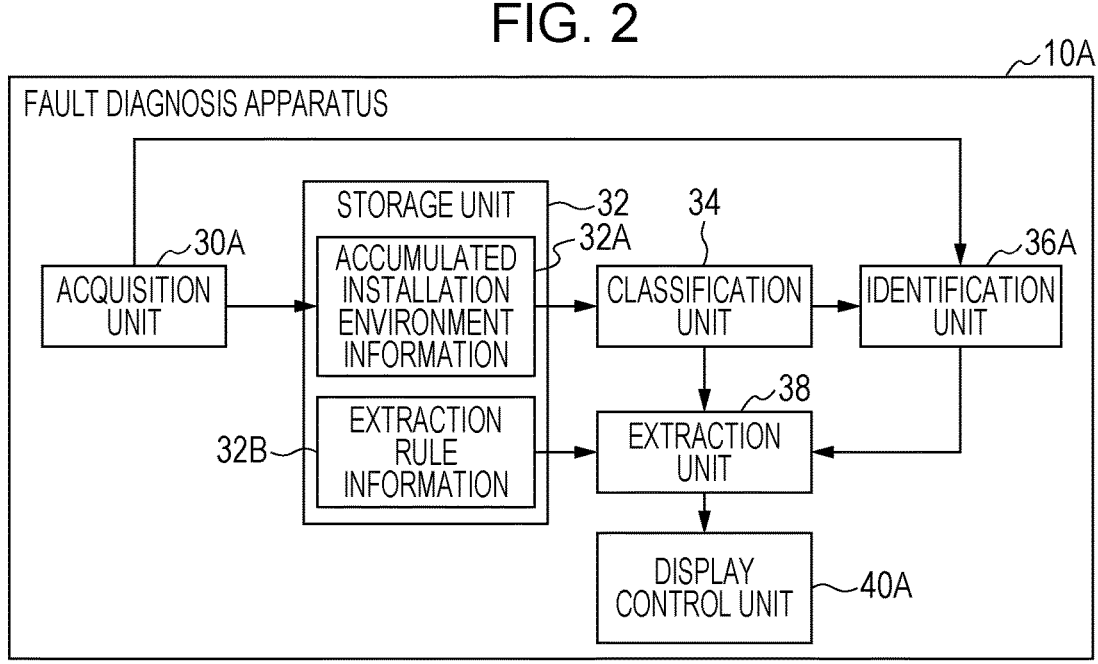
FIG. 2 is a functional block diagram illustrating an example of a functional configuration of a fault diagnosis apparatus according to a first embodiment.

Next, a functional configuration of the fault diagnosis apparatus 10A will be described with reference to FIG. 2. The fault diagnosis apparatus 10A according to this embodiment is configured as a server. As illustrated in FIG. 2, the fault diagnosis apparatus 10A includes an acquisition unit 30A, a storage unit 32, a classification unit 34, an identification unit 36A, an extraction unit 38, and a display control unit 40A. In this embodiment, extraction rule information 32B described below is input in advance by the maintenance person or the like and is stored in the storage unit 32.

The acquisition unit 30A according to this embodiment acquires, for each of the medical devices 20 placed in each facility 18, identification information that uniquely identifies the medical device 20 and installation environment information including a plurality of items about an installation environment in which the medical device 20 is installed. Specifically, as an example, the maintenance person inputs, to the management device 22 in each facility 18, identification information and installation environment information of the medical devices 20 in the corresponding facility 18. The identification information and the installation environment information are input for each of the medical devices 20 regardless of whether the medical device 20 is operating correctly.

Then, each management device 22 periodically transmits the identification information and installation environment information input by the maintenance person in association with each other to the fault diagnosis apparatus 10A via the network 16. The maintenance person inputs installation environment information to the management device 22 each time an installation environment indicated by the installation environment information is changed.

Figures 3, 4:
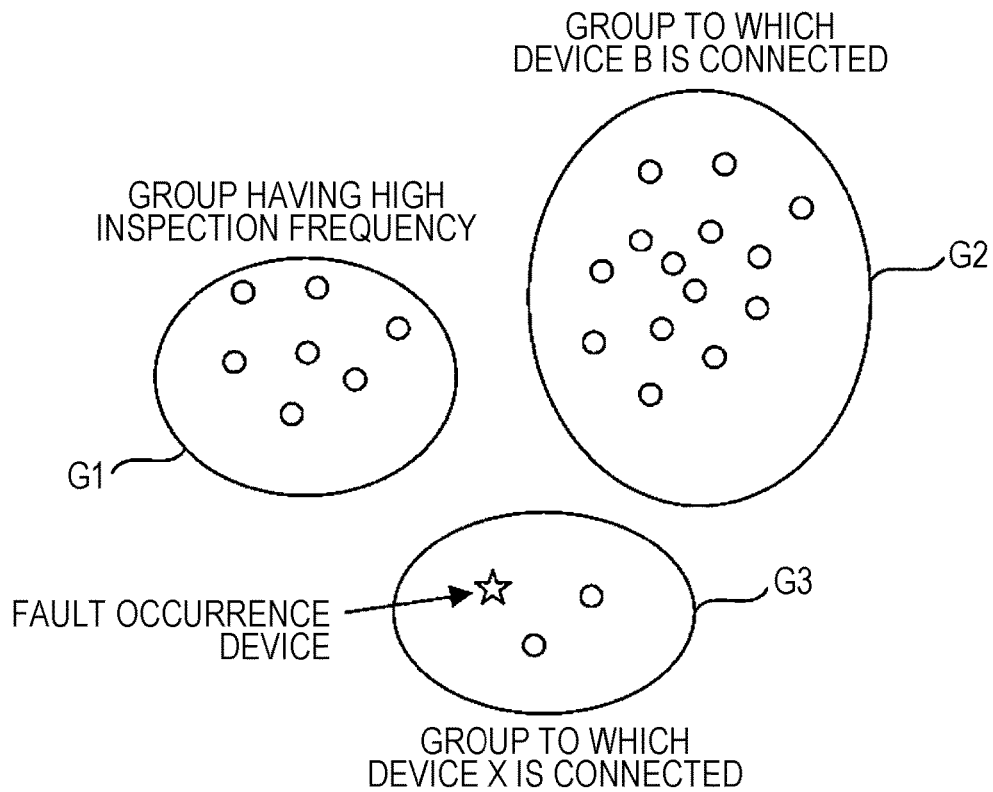
FIG. 3 is a schematic diagram illustrating an example of accumulated installation environment information according to the embodiments.
FIG. 4 is a schematic diagram illustrating an example of a processing result obtained by a classification unit, an identification unit, and an extraction unit according to the first embodiment and a second embodiment.

The acquisition unit 30A acquires the identification information and installation environment information transmitted in the way described above, and stores the acquired identification information and installation environment information in the storage unit 32 in association with each other as accumulated installation environment information 32A. FIG. 3 illustrates an example of the accumulated installation environment information 32A.

As illustrated in FIG. 3, in this embodiment, a unique serial number assigned to each of the medical devices 20 is used as identification information. In this embodiment, information concerning hardware (hereinafter referred to as "hardware information") of the corresponding medical device 20 and information concerning software (hereinafter referred to as "software information") of the corresponding medical device 20 are included in the installation environment information. In this embodiment, furthermore, information concerning maintenance (hereinafter referred to as "maintenance information") of the corresponding medical device 20 is also included in the installation environment information.

As illustrated in FIG. 3, the hardware information according to this embodiment includes device type information indicating the types of connected devices to which the corresponding medical device 20 is connected. Although not illustrated in FIG. 3 to avoid complexity, the hardware information further includes, for example, information concerning a hardware configuration such as the model number of a CPU (Central Processing Unit) mounted in the corresponding medical device 20, and so on.

The software information according to this embodiment includes the version of a software module A installed in the corresponding medical device 20. Although not illustrated in FIG. 3 to avoid complexity, the software information further includes, for example, information indicating the version and type of an OS (Operating System) installed in the corresponding medical device 20. The software information further includes, for example, information concerning a software configuration such as the versions of software modules other than the software module A installed in the corresponding medical device 20.

The maintenance information according to this embodiment includes fault frequency and inspection frequency. Although not illustrated in FIG. 3 to avoid complexity, the maintenance information further includes information concerning maintenance, such as the total period taken for the maintenance performed on the corresponding medical device 20.

In this embodiment, the fault frequency indicates the number of times faults have occurred in the corresponding medical device 20 since the medical device 20 was started to be used. However, this is not limiting, and information concerning the frequency of faults, such as the average value of time intervals at which faults occur, may be used.

In this embodiment, the inspection frequency indicates the number of times the corresponding medical device 20 has been inspected since the medical device 20 was started to be used. However, this is not limiting, and information concerning the frequency of inspections, such as time intervals at which regular inspections occur, may be used.

In the following, a description will be given of a case where four items, namely, connected devices included in the hardware information, the version of the software module A included in the software information, and the fault frequency and the inspection frequency included in the maintenance information, are used as installation environment information to avoid complexity. In the following, furthermore, a description will be given of a case where, as an example, the four items described above are possible causes of a fault that occurs in the medical devices 20.

The classification unit 34 according to this embodiment classifies the medical devices 20 into a plurality of groups (so-called clusters) on the basis of the installation environment information acquired by the acquisition unit 30A. A clustering technique such as the k-means method is applied to this classification. Specifically, for example, the classification unit 34 uses each item in the installation environment information in the accumulated installation environment information 32A as a feature quantity and generates a feature vector having the same number of dimensions as the number of feature quantities.

In this embodiment, a description is given of a case where the feature quantities corresponding to the four items described above, which are possible causes of a fault, are used as feature quantities to be used for generating a feature vector. However, this is not limiting. For example, the maintenance person may select a feature quantity to be used for generating a feature vector each time they perform fault diagnosis. In this case, for example, an embodiment or the like is exemplarily illustrated in which the maintenance person selects a plurality of items other than the software information as feature quantities when they can determine that the fault is not caused by software on the basis of log information or the like of the medical device 20 in which the fault has occurred.

The classification unit 34 then classifies the medical devices 20 into a plurality of groups by using the generated feature vector in accordance with clustering. The groups generated here represent a set of medical devices 20 having similar installation environments that are indicated by the installation environment information of the items corresponding to the feature quantities used for generating the feature vector. The groups obtained as a result of clustering are also referred to as clusters, which are consistently represented as "groups" here.

The identification unit 36A according to this embodiment identifies to which group among the plurality of groups generated by the classification unit 34 the medical device 20 in which a fault to be diagnosed has occurred (hereinafter referred to as the "fault occurrence device 20") belongs. Specifically, the identification unit 36A identifies the group to which the fault occurrence device 20 belongs (hereinafter referred to as "belonging group") by using the serial number of the fault occurrence device 20.

The extraction unit 38 according to this embodiment extracts an item in the installation environment information representing a feature of the belonging group identified by the identification unit 36A, the feature being different from that of the other groups. Specifically, the extraction unit 38 extracts a typical feature that typifies the belonging group (hereinafter referred to as a "typical feature") as the item in the installation environment information in accordance with an extraction rule indicated by the extraction rule information 32B.

The extraction rule according to this embodiment is a rule in which, as an example, a difference between an average value of each feature quantity of the belonging group and each corresponding feature quantity of the groups other than the belonging group is calculated for each feature and a feature corresponding to a feature quantity having the largest absolute value of the difference obtained as a result of calculation is used as a typical feature of the belonging group. Accordingly, the extraction unit 38 extracts the feature corresponding to the feature quantity having the largest absolute value as the typical feature of the belonging group.

FIG. 4 illustrates an example of a state in which a plurality of pieces of installation environment information to be classified by the classification unit 34 are each mapped to one point on a common X-Y coordinate plane as a feature vector for each corresponding medical device 20. In FIG. 4, a state is illustrated in which, for each of the groups obtained by the classification unit 34, points belonging to the same group are surrounded by a common circular line and a typical feature extracted by the extraction unit 38 is depicted near the corresponding circular line. Circles in FIG. 4 each indicate one of the medical devices 20, and a star in FIG. 4 indicates the fault occurrence device 20. In FIG. 4, a state is also illustrated in which, as an example, the medical devices 20 are classified into three groups, namely, groups G1 to G3, by the classification unit 34.

In FIG. 4, a state is also illustrated in which, as an example, the fault occurrence device 20 is identified as belonging to the group G3 by the identification unit 36A. In FIG. 4, a state is also illustrated in which "being connected to device X" is extracted as a typical feature of the group G3 to which the fault occurrence device 20 belongs. In FIG. 4, furthermore, the typical feature of the group G1 is "having high inspection frequency", and the typical feature of the group G2 is "being connected to device B".

As illustrated in FIG. 4, the medical devices 20 corresponding to installation environment information having a comparatively high similarity of feature vectors are classified in the same group.

The display control unit 40A according to this embodiment performs control to cause a display unit to display an extraction result obtained by the extraction unit 38. Specifically, as an example, the display control unit 40A transmits display information including the typical feature extracted by the extraction unit 38, as a possible cause of occurrence of the fault in the fault occurrence device 20, to the maintenance-person terminal 26 that is being used by the maintenance person who is performing maintenance on the fault occurrence device 20.

The term "display", as used herein, includes not only visible display using a display device such as a display but also audible display using an audio reproduction device such as a speaker and permanent visible display using an image forming device such as a printer.

Next, a configuration of a main part of an electrical system of the fault diagnosis apparatus 10A according to this embodiment will be described with reference to FIG. 5.

Figure 5:
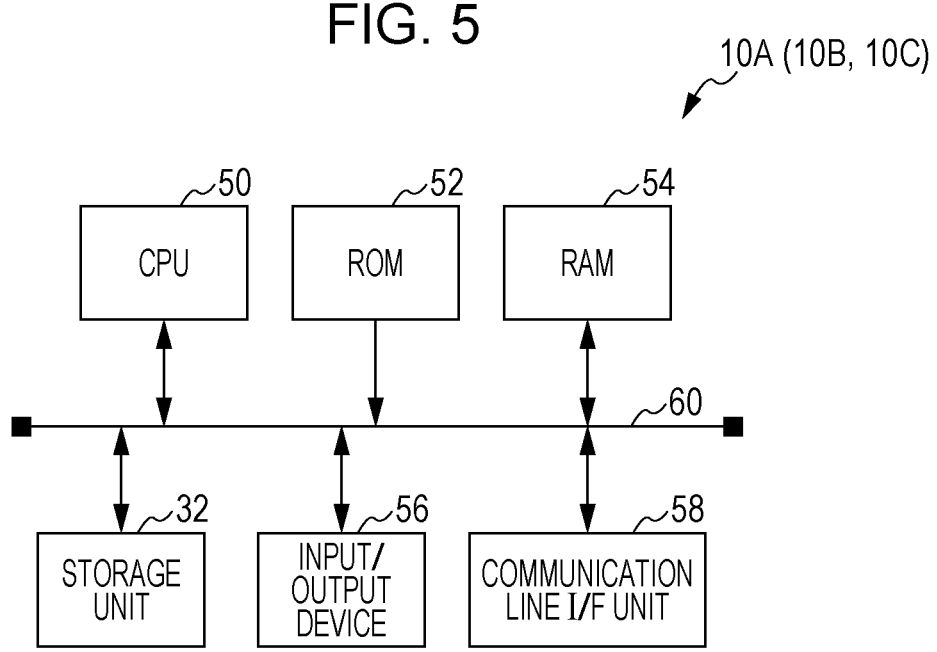
FIG. 5 is a block diagram illustrating an example of a configuration of a main part of an electrical system of the fault diagnosis apparatus according to the embodiments.

As illustrated in FIG. 5, the fault diagnosis apparatus 10A according to this embodiment includes a CPU 50 that controls the entire operation of the fault diagnosis apparatus 10A, and a ROM (Read Only Memory) 52 having stored therein in advance various programs, various parameters, and so on. The fault diagnosis apparatus 10A further includes a RAM (Random Access Memory) 54 used as a work area or the like when the CPU 50 executes various programs, and a non-volatile storage unit 32 such as a flash memory.

The fault diagnosis apparatus 10A further includes an input/output device 56 including a display device such as a display and an input device such as a mouse and a keyboard. The fault diagnosis apparatus 10A further includes a communication line I/F (Interface) unit 58 that is connected to the network 14 described above to transmit and receive communication data to and from an external device.

The individual components, namely, the CPU 50, the ROM 52, the RAM 54, the storage unit 32, the input/output device 56, and the communication line I/F unit 58, are connected to one another via a bus 60.

With the configuration described above, in the fault diagnosis apparatus 10A according to this embodiment, the CPU 50 performs access to the ROM 52, the RAM 54, and the storage unit 32 and transmission and reception of communication data to and from an external device via the communication line I/F unit 58. In the fault diagnosis apparatus 10A, furthermore, the CPU 50 performs acquisition of various types of instruction information via the input/output device 56 and display of various types of information on the input/output device 56.

Figure 6:
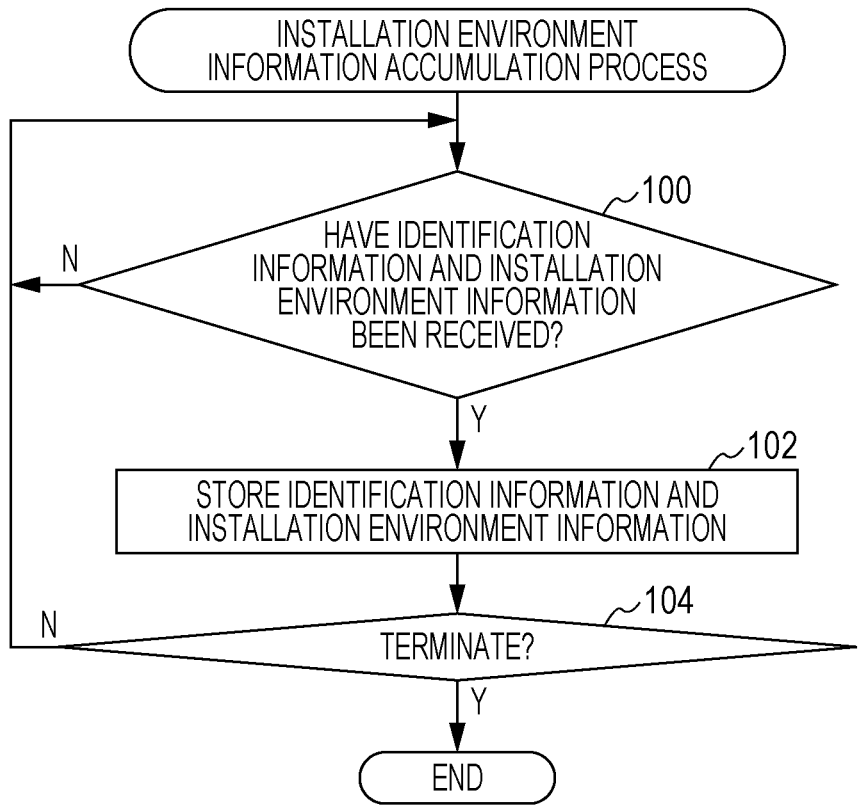
FIG. 6 is a flowchart illustrating a process flow of an installation environment information accumulation process program according to the embodiments.

Next, an effect of the fault diagnosis apparatus 10A according to this embodiment will be described with reference to FIG. 6 and FIG. 7. FIG. 6 is a flowchart illustrating a process flow of an installation environment information accumulation process program that is executed by the CPU 50 when a power switch of the fault diagnosis apparatus 10A is turned on. The installation environment information accumulation process program is installed in the ROM 52 in advance.

Figure 7:
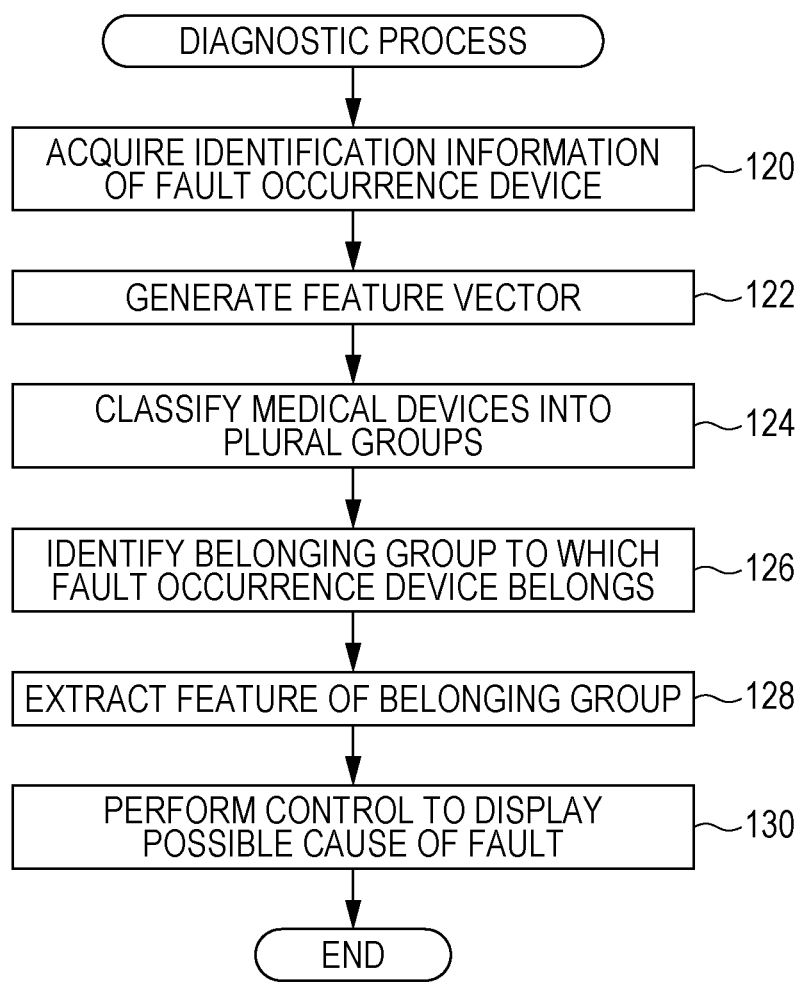
FIG. 7 is a flowchart illustrating a process flow of a diagnostic process program according to the first embodiment.

FIG. 7 is a flowchart illustrating a process flow of a diagnostic process program that is executed by the CPU 50 when identification information of the fault occurrence device 20 and a diagnostic instruction for diagnosing a fault are received. The identification information and the diagnostic instruction are transmitted to the fault diagnosis apparatus 10A by the maintenance person operating the maintenance-person terminal 26 when, for example, a fault has occurred in any one of the medical devices 20. The diagnostic process program is installed in the ROM 52 in advance. The CPU 50 executes the installation environment information accumulation process program and the diagnostic process program, thereby allowing the CPU 50 to function as the acquisition unit 30A, the classification unit 34, the identification unit 36A, the extraction unit 38, and the display control unit 40A described above.

As described above, each management device 22 periodically transmits identification information (in this embodiment, the serial number) and installation environment information that are input by the maintenance person in association with each other to the fault diagnosis apparatus 10A via the network 16. Thus, in step 100 in FIG. 6, the acquisition unit 30A waits for identification information and installation environment information to be received. When the acquisition unit 30A receives identification information and installation environment information, an affirmative determination is obtained in step 100 and then the process proceeds to step 102.

In step 102, the acquisition unit 30A stores the received identification information and installation environment information in the storage unit 32 in association with each other as the accumulated installation environment information 32A (see also FIG. 3). It should be noted that, in step 102, if the accumulated installation environment information 32A already includes a record corresponding to the received identification information, the acquisition unit 30A updates the installation environment information of the record corresponding to the received identification information.

Then, in step 104, the acquisition unit 30A determines whether a timing determined in advance as the timing of termination of the installation environment information accumulation process has been reached. If a negative determination is obtained in this determination, the acquisition unit 30A returns to step 100, whereas if an affirmative determination is obtained in this determination, this installation environment information accumulation process ends. In this embodiment, the timing at which the power switch of the fault diagnosis apparatus 10A is turned off is used as the termination timing. However, this is not limiting. For example, any other timing such as the timing at which the maintenance person or the like inputs an instruction to terminate this installation environment information accumulation process may be used as the termination timing.

On the other hand, in step 120 in FIG. 7, the acquisition unit 30A acquires the received identification information of the fault occurrence device 20. In step 122, as described above, by using the accumulated installation environment information 32A stored in the storage unit 32 through the installation environment information accumulation process, the classification unit 34 uses each item in the installation environment information in the accumulated installation environment information 32A as a feature quantity and generates a feature vector having the same number of dimensions as the number of feature quantities.

Then, in step 124, as described above, the classification unit 34 classifies the medical devices 20 into a plurality of groups by using the feature vector generated in step 122. Then, in step 126, the identification unit 36A identifies a belonging group to which the fault occurrence device 20 belongs from among the plurality of groups generated in step 124 by using the identification information acquired in step 120.

Then, in step 128, as described above, the extraction unit 38 extracts a typical feature of the belonging group identified in step 126. Then, in step 130, as described above, the display control unit 40A transmits, as a possible cause of occurrence of the fault in the fault occurrence device 20, display information including the typical feature extracted in step 128 to the maintenance-person terminal 26. Then, this diagnostic process ends.

Figures 8, 9:
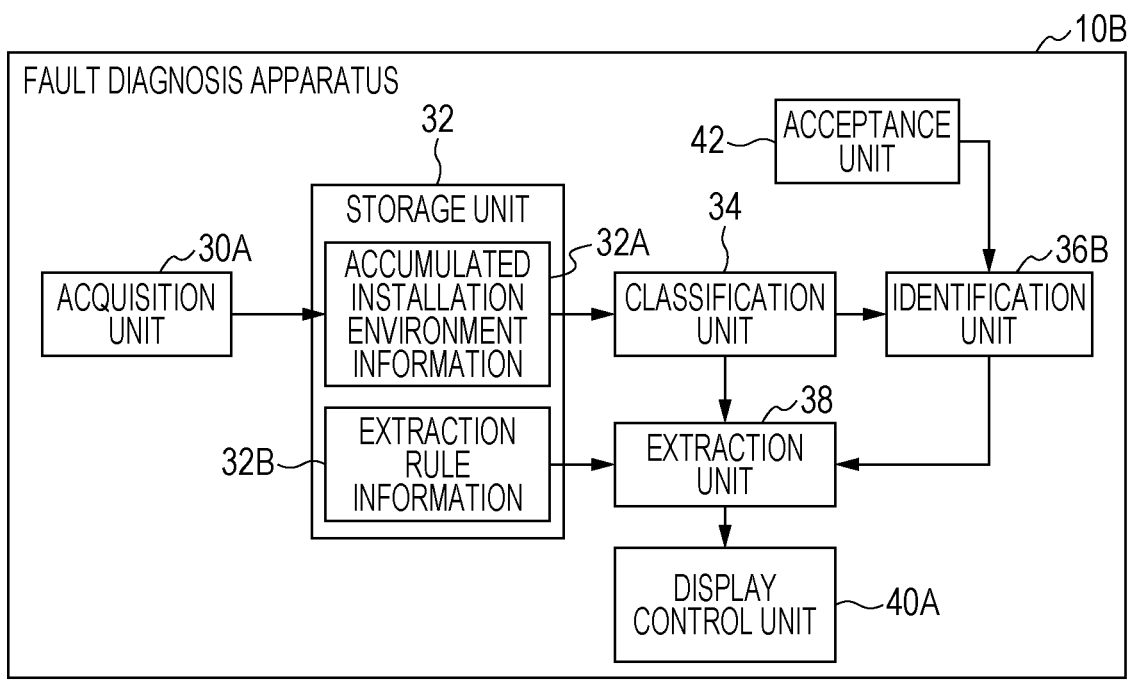
FIG. 8 is a schematic diagram illustrating an example of a diagnostic result display screen according to the first embodiment and the second embodiment.
FIG. 9 is a functional block diagram illustrating an example of a functional configuration of a fault diagnosis apparatus according to the second embodiment.

Upon receipt of the display information transmitted in step 130, the maintenance-person terminal 26 displays a diagnostic result display screen indicated by the received display information on a display of the maintenance-person terminal 26. FIG. 8 illustrates an example of the diagnostic result display screen. As illustrated in FIG. 8, the diagnostic result display screen according to this embodiment is displayed in such a manner that information indicating the typical feature is highlighted (in the example illustrated in FIG. 8, underlined).

The maintenance person refers to the diagnostic result display screen to understand a possible cause of the fault in the fault occurrence device 20 and then identifies the cause of the fault in the fault occurrence device 20. For example, as illustrated in FIG. 8, if the typical feature of the fault occurrence device 20 is being connected to device X, the maintenance person examines the state of components of the fault occurrence device 20 that are related to connection with device X. In this case, the maintenance person further refers to the log information or the like of the fault occurrence device 20 to examine whether data transmitted from device X to the fault occurrence device 20 includes unauthorized data. This can reduce the period taken for the maintenance person to identify the cause of the fault in the fault occurrence device 20.

The diagnostic result display screen is not limited to the example illustrated in FIG. 8. In an embodiment, for example, the display control unit 40A may transmit display information corresponding to the schematic diagram illustrated in FIG. 4 to the maintenance-person terminal 26. In this exemplary embodiment, the maintenance person refers to the diagnostic result display screen to understand a result of classification using clustering and also understand to which group the fault occurrence device 20 belongs. In an embodiment, furthermore, the display control unit 40A may transmit display information corresponding to both the character string including the typical feature illustrated in FIG. 8 and the schematic diagram illustrated in FIG. 4 to the maintenance-person terminal 26.

As described above, according to this embodiment, an acquisition unit (the acquisition unit 30A) acquires, for each of a plurality of devices (the medical devices 20), installation environment information including a plurality of items about an installation environment in which each of the plurality of devices is installed. According to this embodiment, furthermore, a classification unit (the classification unit 34) classifies the plurality of devices into a plurality of groups on the basis of the installation environment information. According to this embodiment, moreover, an extraction unit (the extraction unit 38) extracts an item in the installation environment information representing a feature of a group to which a device in which a fault has occurred among the plurality of devices belongs, the feature being different from that of the other groups. In addition, according to this embodiment, a display control unit (the display control unit 40A) performs control to cause a display unit to display an extraction result obtained by the extraction unit. This can assist an operation of identifying the cause of a fault in a device in which the fault has occurred.

That is, in some cases, it may be difficult for a maintenance person who, for example, fixes a fault that has occurred in a device to know installation environment information of the device. Even if installation environment information can be found, it may be difficult to determine whether the installation environment is characteristic. According to this embodiment, thus, installation environment information is acquired for each of a plurality of devices, the plurality of devices are classified into a plurality of groups, and an item in the installation environment information representing a feature of a group to which a device in which a fault has occurred belongs is extracted. The extracted item is displayed to the maintenance person to inform the maintenance person of a characteristic item in the installation environment information for the device. This can assist an operation of identifying the cause of a fault in a device in which the fault has occurred.

Second Embodiment

In the first embodiment, an exemplary embodiment has been described in which a process for classifying the medical devices 20 into a plurality of groups is performed when fault diagnosis is performed. In contrast, this second embodiment is different from the first embodiment in that the process for classifying the medical devices 20 into a plurality of groups is periodically performed in advance.

A connection configuration of a fault diagnosis apparatus 10B, medical devices 20, and management devices 22 according to this embodiment is similar to the connection configuration of the fault diagnosis apparatus 10A, the medical devices 20, and the management devices 22 according to the first embodiment (see FIG. 1) described above, and a description thereof is thus omitted here. A configuration of a main part of an electrical system of the fault diagnosis apparatus 10B according to this embodiment is also similar to the configuration of the main part of the electrical system of the fault diagnosis apparatus 10A according to the first embodiment (see FIG. 5) described above, and a description thereof is thus omitted here.

First, a functional configuration of the fault diagnosis apparatus 10B according to this embodiment will be described with reference to FIG. 9. In FIG. 9, constituent elements having the same functions as those in FIG. 2 are assigned the same numerals as those in FIG. 2, and a description thereof is omitted.

As illustrated in FIG. 9, the fault diagnosis apparatus 10B further includes an acceptance unit 42. The acceptance unit 42 according to this embodiment accepts installation environment information of the fault occurrence device 20 when fault diagnosis is performed. Specifically, as an example, the maintenance person transmits the installation environment information of the fault occurrence device 20 to the fault diagnosis apparatus 10B by using the maintenance-person terminal 26. Then, the acceptance unit 42 accepts the installation environment information transmitted from the maintenance-person terminal 26. The installation environment information of the fault occurrence device 20 may be input directly to the fault diagnosis apparatus 10B.

An identification unit 36B according to this embodiment identifies a belonging group to which the fault occurrence device 20 belongs on the basis of the installation environment information accepted by the acceptance unit 42. Specifically, the identification unit 36B classifies the fault occurrence device 20 in any one of a plurality of groups generated by the classification unit 34 as a result of classification on the basis of the installation environment information of the fault occurrence device 20, which is similar to classification performed by the classification unit 34 using clustering. That is, as a result of this classification, the identification unit 36B identifies a group in which the fault occurrence device 20 is classified as being a belonging group.

Figure 10:
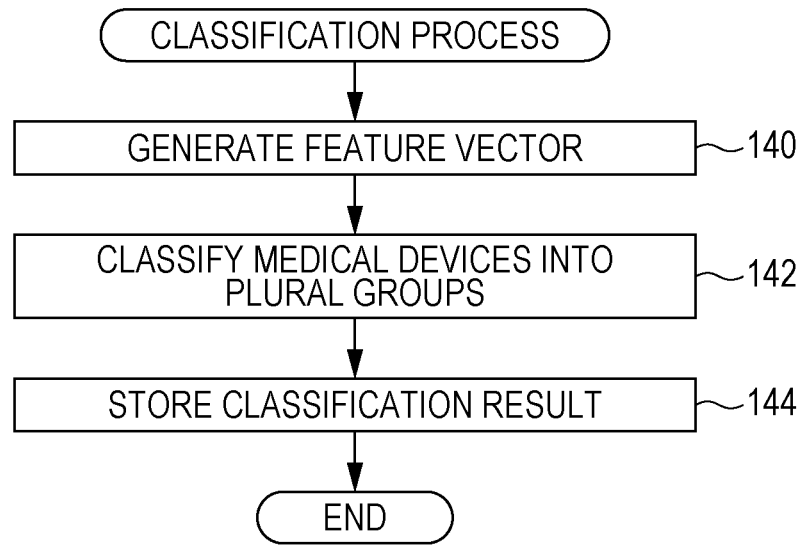
FIG. 10 is a flowchart illustrating a process flow of a classification process program according to the second embodiment.

Next, an effect of the fault diagnosis apparatus 10B according to this embodiment will be described with reference to FIG. 10 and FIG. 11. An installation environment information accumulation process according to this embodiment is similar to the installation environment information accumulation process according to the first embodiment (see FIG. 6) described above, and a description thereof is thus omitted here. FIG. 10 is a flowchart illustrating a process flow of a classification process program that is executed by the CPU 50 at predetermined time intervals. The classification process program is installed in the ROM 52 in advance. Alternatively, the classification process program may be executed at each timing at which the accumulated installation environment information 32A is updated, for example.

Figure 11:
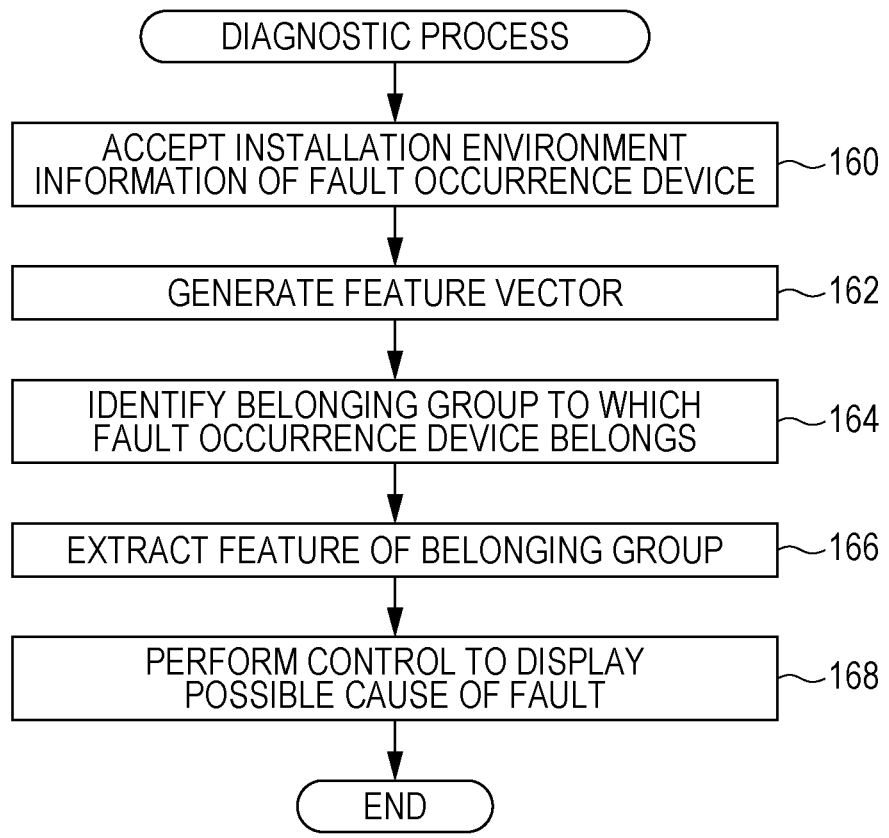
FIG. 11 is a flowchart illustrating a process flow of a diagnostic process program according to the second embodiment.

FIG. 11 is a flowchart illustrating a process flow of a diagnostic process program that is executed by the CPU 50 when installation environment information of the fault occurrence device 20 and a diagnostic instruction for diagnosing a fault are received. The installation environment information and the diagnostic instruction are transmitted to the fault diagnosis apparatus 10B by the maintenance person operating the maintenance-person terminal 26 when, for example, a fault has occurred in any one of the medical devices 20. The diagnostic process program is installed in the ROM 52 in advance. The CPU 50 executes an installation environment information accumulation process program, the classification process program, and the diagnostic process program, thereby allowing the CPU 50 to function as the acquisition unit 30A, the classification unit 34, the identification unit 36B, the extraction unit 38, the display control unit 40A, and the acceptance unit 42.

In step 140 in FIG. 10, as in step 122, by using the accumulated installation environment information 32A stored in the storage unit 32, the classification unit 34 uses each item in the installation environment information in the accumulated installation environment information 32A as a feature quantity and generates the feature vector described above.

Then, in step 142, as in step 124, the classification unit 34 classifies the medical devices 20 into a plurality of groups by using the feature vector generated in step 140. Then, in step 144, the classification unit 34 stores classification result information indicating the classification result obtained in step 142 in the storage unit 32. Then, this classification process ends.

On the other hand, in step 160 in FIG. 11, the acceptance unit 42 accepts the received installation environment information of the fault occurrence device 20. Then, in step 162, the identification unit 36B uses each item in the installation environment information accepted in step 160 as a feature quantity and generates a feature vector having the same number of dimensions as the number of feature quantities.

Then, in step 164, as described above, the identification unit 36B identifies a belonging group to which the fault occurrence device 20 belongs by using the feature vector generated in step 162 and the classification result information stored in the storage unit 32 through the classification process. Then, in step 166, as in step 128, the extraction unit 38 extracts a typical feature of the belonging group identified in step 164.

Then, in step 168, as in step 130, the display control unit 40A transmits, as a possible cause of occurrence of the fault in the fault occurrence device 20, display information including the typical feature extracted in step 166 to the maintenance-person terminal 26. Then, this diagnostic process ends.

As described above, according to this embodiment, clustering based on installation environment information of the medical devices 20 is performed in advance. This can reduce the period of time taken for a diagnostic process when a fault occurs. According to this embodiment, furthermore, a process for identifying a belonging group is performed on the basis of installation environment information of the fault occurrence device 20. Thus, there is no problem if the accumulated installation environment information 32A includes no identification information.

Third Embodiment

In this third embodiment, an exemplary embodiment will be described in which fault information concerning the types of faults that have previously occurred in the medical devices 20 is also used in the first embodiment described above. A connection configuration of a fault diagnosis apparatus 10C, medical devices 20, and management devices 22 according to this embodiment is similar to the connection configuration of the fault diagnosis apparatus 10A, the medical devices 20, and the management devices 22 according to the first embodiment (see FIG. 1) described above, and a description thereof is thus omitted here. A configuration of a main part of an electrical system of the fault diagnosis apparatus 10C according to this embodiment is also similar to the configuration of the main part of the electrical system of the fault diagnosis apparatus 10A according to the first embodiment (see FIG. 5) described above, and a description thereof is thus omitted here.

Figures 12, 13:
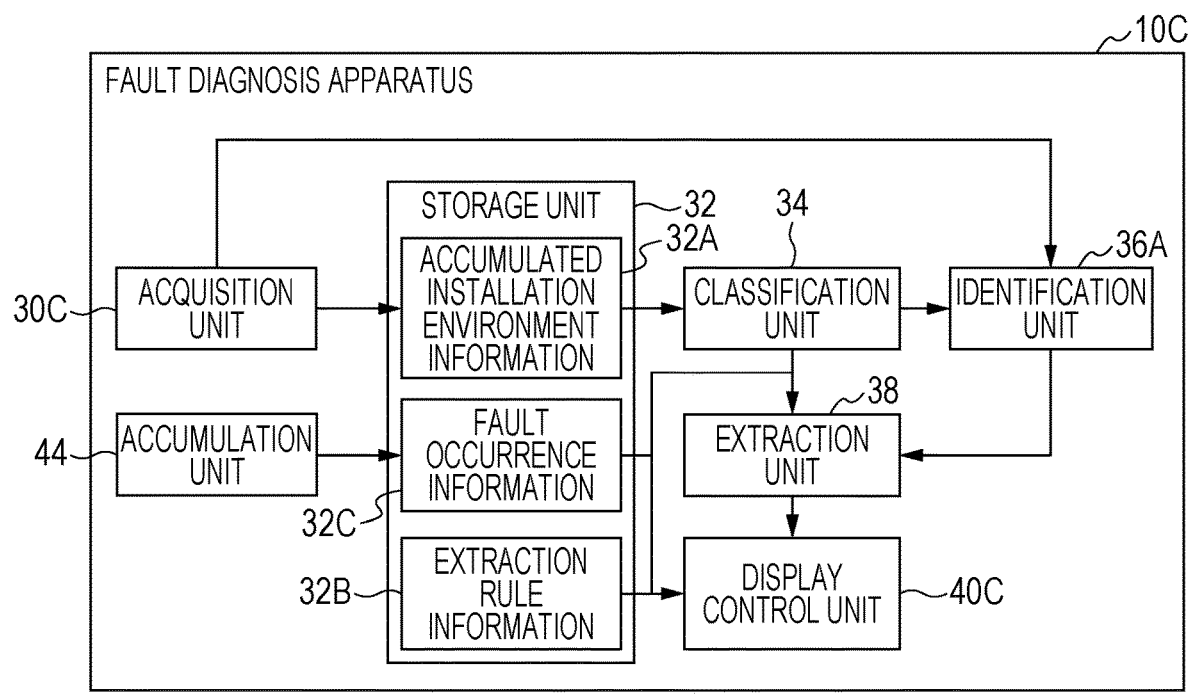
FIG. 12 is a functional block diagram illustrating an example of a functional configuration of a fault diagnosis apparatus according to a third embodiment.
FIG. 13 is a schematic diagram illustrating an example of fault occurrence information according to the third embodiment.

First, a functional configuration of the fault diagnosis apparatus 10C according to this embodiment will be described with reference to FIG. 12. In FIG. 12, constituent elements having the same functions as those in FIG. 2 are assigned the same numerals as those in FIG. 2, and a description thereof is omitted.

As illustrated in FIG. 12, the fault diagnosis apparatus 10C further includes an accumulation unit 44. The accumulation unit 44 according to this embodiment receives fault information concerning the types of faults that have occurred in the medical devices 20, and identification information of the corresponding medical devices 20. The fault information and the identification information are transmitted to the fault diagnosis apparatus 10C by the maintenance person operating the maintenance-person terminal 26 when, for example, a fault has occurred in any one of the medical devices 20.

Further, the accumulation unit 44 accumulates the received identification information and fault information in the storage unit 32 in association with each other as fault occurrence information 32C. FIG. 13 illustrates an example of the fault occurrence information 32C.

As illustrated in FIG. 13, the fault information according to this embodiment includes fault identification information identifying a type of fault, and time-and-date information indicating the time and date when the fault occurred. Although not illustrated in FIG. 13 to avoid complexity, the fault information further includes, for example, the cumulative number of times the type of fault corresponding to the fault identification information has occurred in the medical device 20 corresponding to the identification information, and so on.

On the other hand, an acquisition unit 30C according to this embodiment further acquires identification information and fault identification information of the fault occurrence device 20. Specifically, as an example, the maintenance person identifies fault identification information by using the log information or the like of the fault occurrence device 20 and transmits the identification information and the fault identification information of the fault occurrence device 20 to the fault diagnosis apparatus 10C by using the maintenance-person terminal 26. The identification information and the fault identification information of the fault occurrence device 20 may be transmitted from the fault occurrence device 20 to the fault diagnosis apparatus 10C via the network 16 or may be directly input to the fault diagnosis apparatus 10C by the maintenance person or the like.

Further, a display control unit 40C according to this embodiment performs control to display groups classified by the classification unit 34 in such a manner that, on the basis of the fault occurrence information 32C accumulated by the accumulation unit 44, the medical device or devices 20 in which the same type as the type of fault indicated by the fault identification information acquired by the acquisition unit 30C has occurred are recognizable.

Figure 14:
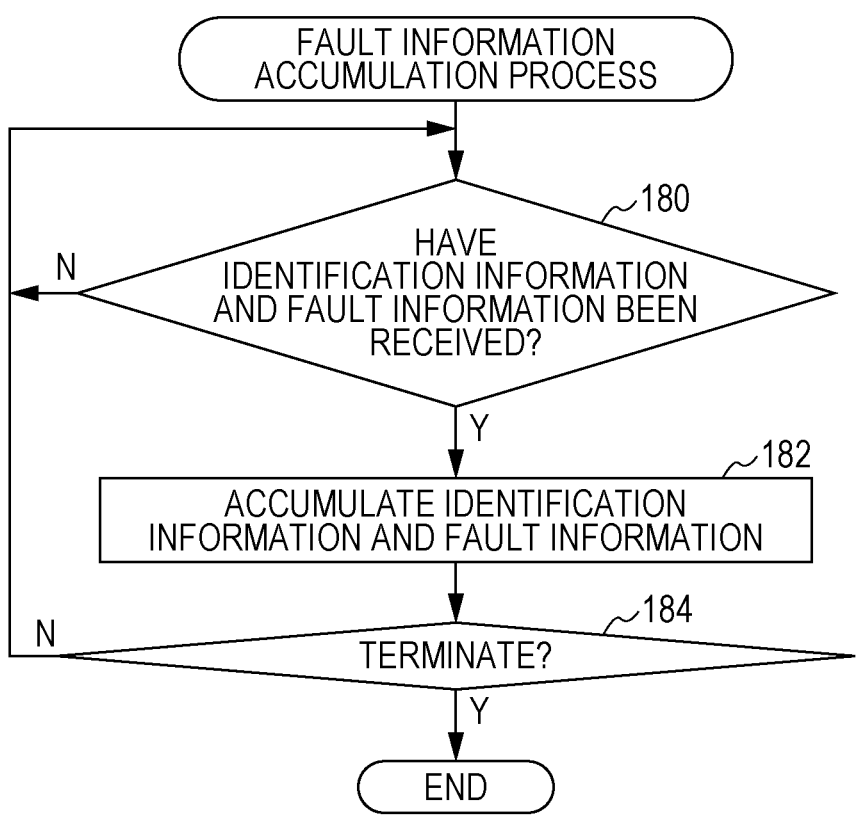
FIG. 14 is a flowchart illustrating a process flow of a fault information accumulation process program according to the third embodiment.

Next, an effect of the fault diagnosis apparatus 10C according to this embodiment will be described with reference to FIG. 14 and FIG. 15. An installation environment information accumulation process according to this embodiment is similar to the installation environment information accumulation process according to the first embodiment (see FIG. 6) described above, and a description thereof is thus omitted here. FIG. 14 is a flowchart illustrating a process flow of a fault information accumulation process program that is executed by the CPU 50 when a power switch of the fault diagnosis apparatus 10C is turned on. The fault information accumulation process program is installed in the ROM 52 in advance.

Figure 15:
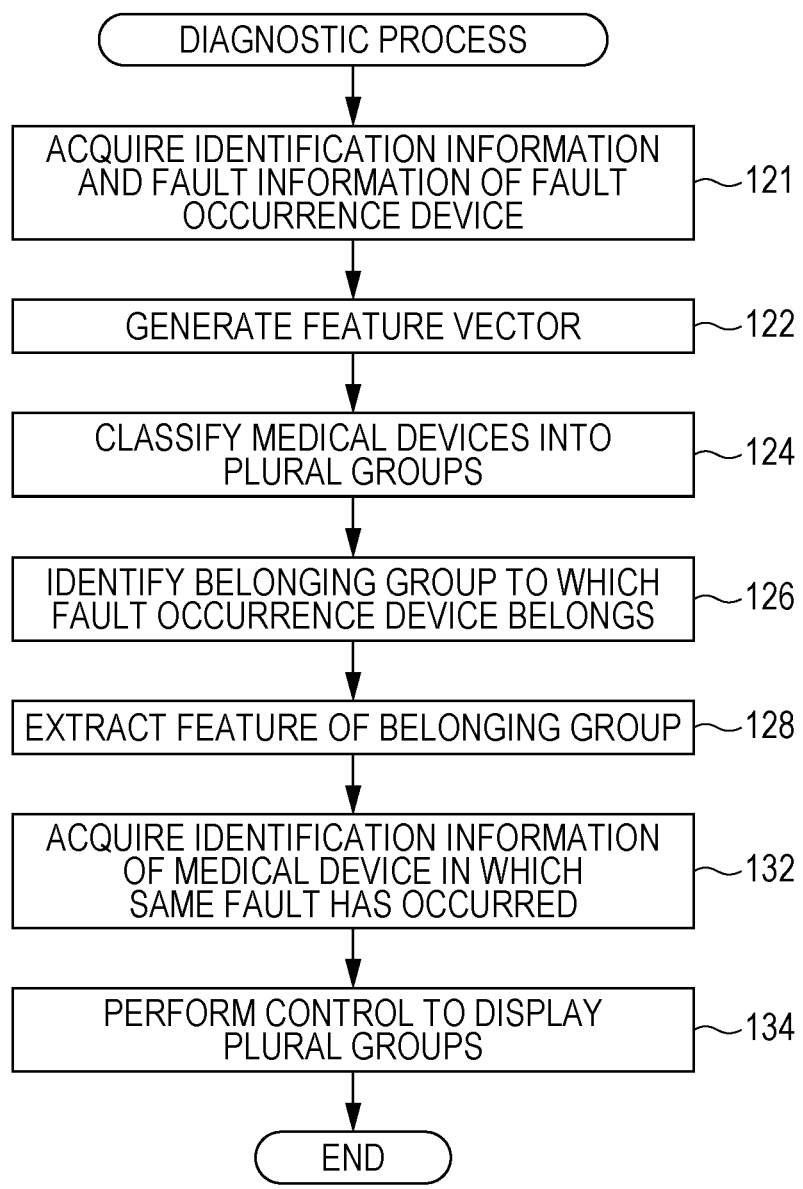
FIG. 15 is a flowchart illustrating a process flow of a diagnostic process program according to the third embodiment.

FIG. 15 is a flowchart illustrating a process flow of a diagnostic process program that is executed by the CPU 50 when identification information and fault identification information of the fault occurrence device 20 and a diagnostic instruction for diagnosing a fault are received. The identification information and fault identification information and the diagnostic instruction for diagnosing a fault are transmitted to the fault diagnosis apparatus 10C by the maintenance person operating the maintenance-person terminal 26 when, for example, a fault has occurred in any one of the medical devices 20. The diagnostic process program is installed in the ROM 52 in advance.

In FIG. 15, the steps in which the same processes as those in FIG. 7 are executed are assigned the same step numbers as those in FIG. 7, and a description thereof is omitted. As illustrated in FIG. 15, a diagnostic process according to this embodiment is different from the diagnostic process according to the first embodiment described above in that step 121 is executed instead of step 120. The diagnostic process according to this embodiment is further different from the diagnostic process according to the first embodiment described above in that step 132 and step 134 are executed instead of step 130. In addition, the CPU 50 executes an installation environment information accumulation process program, the fault information accumulation process program, and the diagnostic process program, thereby allowing the CPU 50 to function as the acquisition unit 30C, the classification unit 34, the identification unit 36A, the extraction unit 38, the display control unit 40C, and the accumulation unit 44 described above.

As described above, when a fault has occurred in any one of the medical devices 20, the maintenance person operates the maintenance-person terminal 26 to transmit fault information and identification information to the fault diagnosis apparatus 10C. Thus, in step 180 in FIG. 14, the accumulation unit 44 waits for identification information and fault information to be received. When the accumulation unit 44 receives identification information and fault information, an affirmative determination is obtained in step 180 and then the process proceeds to step 182.

In step 182, the accumulation unit 44 accumulates the identification information and fault information received in step 180 in the storage unit 32 in association with each other as the fault occurrence information 32C (see also FIG. 13). Then, in step 184, the accumulation unit 44 determines whether a timing determined in advance as the timing of termination of the fault information accumulation process has been reached. If a negative determination is obtained in this determination, the accumulation unit 44 returns to step 180, whereas if an affirmative determination is obtained in this determination, this fault information accumulation process ends. In this embodiment, the timing at which the power switch of the fault diagnosis apparatus 10C is turned off is used as the termination timing. However, this is not limiting. For example, any other timing such as the timing at which the maintenance person or the like inputs an instruction to terminate this fault information accumulation process may be used as the termination timing.

On the other hand, in step 121 in FIG. 15, the acquisition unit 30C acquires the received identification information and fault identification information of the fault occurrence device 20. Thereafter, in step 132, the display control unit 40C refers to the fault occurrence information 32C accumulated through the fault information accumulation process and acquires identification information of the medical device or devices 20 in which the same type of fault as the type of fault indicated by the fault identification information acquired in step 121 has previously occurred.

Then, in step 134, the display control unit 40C transmits, to the maintenance-person terminal 26, display information for causing the plurality of groups generated in step 124 to be displayed in such a manner that the medical device or devices 20 indicated by the identification information acquired in step 132 are recognizable. The display information to be transmitted by the display control unit 40C is information capable of identifying the fault occurrence device or devices 20, which correspond to the identification information acquired in step 121, and the display information further includes the typical feature extracted in step 128 in the display information. After the display control unit 40C transmits the display information to the maintenance-person terminal 26, this diagnostic process ends.

Upon receipt of the display information transmitted in step 134, the maintenance-person terminal 26 displays a diagnostic result display screen indicated by the received display information on the display of the maintenance-person terminal 26. FIG. 16 illustrates an example of the diagnostic result display screen. As illustrated in FIG. 16, the diagnostic result display screen according to this embodiment displays a schematic diagram of a state in which a plurality of pieces of installation environment information to be classified by the classification unit 34 are each mapped to one point on a common X-Y coordinate plane as a feature vector for each corresponding medical device 20.

In FIG. 16, a state is also illustrated in which, for each of the groups obtained by the classification unit 34, points belonging to the same group are surrounded by a common circular line and a typical feature of the belonging group extracted by the extraction unit 38 is depicted near the corresponding circular line. Such display corresponds to an example of displaying a classification result obtained by the classification unit 34 in an identifiable manner for each classified group. The method for displaying a classification result obtained by the classification unit 34 in an identifiable manner for each classified group is not limited to this method, and any display that enables a person skilled in the art who sees display to identify the classification result for each classified group may be used. Circles in FIG. 16 each indicate one of the medical devices 20, and a star in FIG. 16 indicates the fault occurrence device 20. Such display corresponds to an example of displaying a classification result in such a manner that a device in which a fault has occurred can be identified. The method for displaying a classification result in such a manner that a device in which a fault has occurred can be identified is not limited to this method, and any display that enables a person skilled in the art who sees display to identify a device in which a fault has occurred may be used. Triangles in FIG. 16 indicate the medical devices 20 in which the same type of fault as the type of fault that has occurred in the fault occurrence device 20 has previously occurred. Such display corresponds to an example of displaying a plurality of groups in such a manner that devices in which the same type of fault as a type of fault indicated by the fault information acquired by the acquisition unit 30C has occurred are recognizable. The method for displaying a plurality of groups in such a manner that devices in which the same type of fault as a type of fault indicated by the fault information acquired by the acquisition unit 30C has occurred are recognizable is not limited to this method, and any display that enables a person skilled in the art who sees display can recognize devices in which the same type of fault as a type of fault indicated by the fault information acquired by the acquisition unit 30C has occurred may be used. In FIG. 16, a state is further illustrated in which, as an example, the medical devices 20 are classified into three groups by the classification unit 34.

In FIG. 16, a state is further illustrated in which, as an example, "being connected to device X" is extracted as a typical feature of the belonging group to which the fault occurrence device 20 belongs.

The maintenance person can refer to the diagnostic result display screen to understand a possible cause of the fault in the fault occurrence device 20 and then can identify the cause of the fault in the fault occurrence device 20. According to this embodiment, in particular, the maintenance person can understand that the same group as that to which the fault occurrence device 20 belongs includes a comparatively large number of medical devices 20 in which the same type of fault as the type of fault that has occurred in the fault occurrence device 20 has previously occurred. Accordingly, the maintenance person can understand that the probability that "being connected to device X" is the cause of the current fault that has occurred in the fault occurrence device 20 is comparatively high and then can perform an operation of identifying the cause of the fault of the fault occurrence device 20.

In each of the embodiments described above, a description has been given of a case where identification information and installation environment information are transmitted from the management devices 22 to the fault diagnosis apparatus 10A (10B, 10C). However, this is not limiting. In an embodiment, identification information and installation environment information may be transmitted from each of the medical devices 20 to the fault diagnosis apparatus 10A via the network 16, or may be directly input to the fault diagnosis apparatus 10A by the maintenance person or the like. In this exemplary embodiment, each facility 18 may not necessarily be provided with the management device 22.

In each of the embodiments described above, a description has been given of a case where only one typical feature is extracted as a possible cause of the fault in the fault occurrence device 20. However, this is not limiting. In an embodiment, for example, a plurality of features may be extracted as possible causes of the fault in the fault occurrence device 20. As an exemplary embodiment in this case, for example, an embodiment is exemplarily illustrated in which the extraction unit 38 extracts a plurality of features in descending order from a feature corresponding to a feature quantity having the largest absolute value of the difference between the average value of each feature quantity of the belonging group and each corresponding feature quantity of the groups other than the belonging group.

In each of the embodiments described above, furthermore, a description has been given of a case where, as an extraction rule indicated by the extraction rule information 32B, a rule is used in which the feature corresponding to the feature quantity having the largest absolute value is used as a typical feature of the belonging group. However, this is not limiting. In an embodiment, for example, as the extraction rule described above, a rule may be used in which a variance value of each feature quantity of the belonging group is calculated for each feature and a feature corresponding to a feature quantity having the largest variance value is used as a typical feature of the belonging group. In another embodiment, for example, as the extraction rule described above, a rule may be used in which the ratio of a variance value of each feature quantity of the belonging group to a variance value of each feature quantity of all groups is calculated for each feature and a feature corresponding to a feature quantity having the largest ratio of variance values is used as a typical feature of the belonging group. As an exemplary embodiment in these cases, an embodiment may be used in which a plurality of rules are used as extraction rules and a plurality of typical features of the belonging group are each extracted in accordance with one of the plurality of rules.

In this case, furthermore, in an embodiment, a plurality of rules may be set as the extraction rules described above and the maintenance person may select which rule among the plurality of rules to use to extract a typical feature when performing fault diagnosis.

In each of the embodiments described above, furthermore, a description has been given of a case where the medical devices 20 are classified into a plurality of groups by using a single type of feature vector. However, this is not limiting. In an embodiment, for example, a plurality of types of feature vectors obtained by using different items in the installation environment information as feature quantities may be each used to individually classify the medical devices 20 into a plurality of groups. As an exemplary embodiment in this case, an embodiment is exemplarily illustrated in which a typical feature is extracted for each of a plurality of groups to which the fault occurrence device 20 belongs.

In each of the embodiments described above, furthermore, a description has been given of a case where the k-means method is applied to the classification of installation environment information by the classification unit 34. However, this is not limiting. The classification of installation environment information may be performed by using any other non-hierarchical cluster analysis method such as a minimum average variance estimation method or a self-organizing map or by using a hierarchical cluster analysis method such as a shortest distance method, a longest distance method, a group average method, a centroid method, or Ward's method.

In each of the embodiments described above, furthermore, a description has been given of a case where a fault diagnosis apparatus transmits display information corresponding to a diagnostic result display screen to a maintenance-person terminal and the diagnostic result display screen is displayed on a display of the maintenance-person terminal. However, this is not limiting. In an embodiment, for example, the diagnostic result display screen may be displayed on a display of an input/output device of the fault diagnosis apparatus.

In each of the embodiments described above, moreover, a description has been given of a case where a medical device is used as a device to be diagnosed for a fault. However, this is not limiting. In an embodiment, an information processing device such as a computer or any other device such as an image reader or an image forming device may be used as a device to be diagnosed for a fault.

In each embodiment described above, furthermore, the manner in which various programs are stored (installed) in the ROM 52 in advance has been described. However, this is not limiting. The various programs may be provided in the form of being recorded on a recording medium such as a CD-ROM (Compact Disk Read Only Memory), a DVD-ROM (Digital Versatile Disk Read Only Memory), or a USB (Universal Serial Bus) memory. The various programs may be in the form of being downloaded from an external device via a network.

REFERENCE SIGNS LIST 10A, 10B, 10C fault diagnosis apparatus
20 medical device (fault occurrence device)
26 maintenance-person terminal
30A, 30C acquisition unit
32 storage unit
32A accumulated installation environment information
32B extraction rule information
32C fault occurrence information
34 classification unit
36A, 36B identification unit
38 extraction unit
40A, 40C display control unit
42 acceptance unit
44 accumulation unit
50 CPU

What is claimed is:
1. A fault diagnosis apparatus comprising:
an acquisition unit that acquires, for each of a plurality of devices, installation environment information including a plurality of items about an installation environment in which each of the plurality of devices is installed;
a classification unit that classifies the plurality of devices into a plurality of groups on the basis of the installation environment information;
an extraction unit that extracts an item in the installation environment information representing a feature of a group to which a device in which a fault has occurred among the plurality of devices belongs, the feature being different from a feature of other groups; and a display control unit that performs control to cause a display unit to display an extraction result obtained by the extraction unit.

2. The fault diagnosis apparatus according to claim 1, wherein the classification unit performs the classification on the basis of an item in the installation environment information, the item being a possible cause of occurrence of the fault.

3. The fault diagnosis apparatus according to claim 2, wherein the display control unit performs control to cause the display unit to display a classification result obtained by the classification unit in an identifiable manner for each classified group.

4. The fault diagnosis apparatus according to claim 3, wherein the display control unit performs control to cause the display unit to display the classification result in such a manner as to enable the device in which the fault has occurred to be identified.

5. The fault diagnosis apparatus according to claim 4, further comprising:
an accumulation unit that accumulates fault occurrence information in which fault information concerning a type of fault that has occurred in the device and identification information assigned to each of the plurality of devices are associated with each other,
wherein the acquisition unit acquires the fault information of the device in which the fault has occurred, and
wherein the display control unit performs control to cause the display unit to display the plurality of groups in such a manner that, on the basis of the fault occurrence information accumulated by the accumulation unit, a device in which the same type of fault as a type of fault indicated by the fault information acquired by the acquisition unit has occurred is recognizable.

6. The fault diagnosis apparatus according to claim 3, further comprising:
an accumulation unit that accumulates fault occurrence information in which fault information concerning a type of fault that has occurred in the device and identification information assigned to each of the plurality of devices are associated with each other,
wherein the acquisition unit acquires the fault information of the device in which the fault has occurred, and
wherein the display control unit performs control to cause the display unit to display the plurality of groups in such a manner that, on the basis of the fault occurrence information accumulated by the accumulation unit, a device in which the same type of fault as a type of fault indicated by the fault information acquired by the acquisition unit has occurred is recognizable.

7. The fault diagnosis apparatus according to claim 2, further comprising:
an accumulation unit that accumulates fault occurrence information in which fault information concerning a type of fault that has occurred in the device and identification information assigned to each of the plurality of devices are associated with each other,
wherein the acquisition unit acquires the fault information of the device in which the fault has occurred, and
wherein the display control unit performs control to cause the display unit to display the plurality of groups in such a manner that, on the basis of the fault occurrence information accumulated by the accumulation unit, a device in which the same type of fault as a type of fault indicated by the fault information acquired by the acquisition unit has occurred is recognizable.

8. The fault diagnosis apparatus according to claim 2, wherein the installation environment information for each of the plurality of devices includes a plurality of items about at least one of information concerning hardware of a connected device to which the device is connected, information concerning software used in the device, or information concerning maintenance of the device.

9. The fault diagnosis apparatus according to claim 1, wherein the display control unit performs control to cause the display unit to display a classification result obtained by the classification unit in an identifiable manner for each classified group.

10. The fault diagnosis apparatus according to claim 9, wherein the display control unit performs control to cause the display unit to display the classification result in such a manner as to enable the device in which the fault has occurred to be identified.

11. The fault diagnosis apparatus according to claim 10, further comprising:
an accumulation unit that accumulates fault occurrence information in which fault information concerning a type of fault that has occurred in the device and identification information assigned to each of the plurality of devices are associated with each other,
wherein the acquisition unit acquires the fault information of the device in which the fault has occurred, and
wherein the display control unit performs control to cause the display unit to display the plurality of groups in such a manner that, on the basis of the fault occurrence information accumulated by the accumulation unit, a device in which the same type of fault as a type of fault indicated by the fault information acquired by the acquisition unit has occurred is recognizable.

12. The fault diagnosis apparatus according to claim 9, further comprising:
an accumulation unit that accumulates fault occurrence information in which fault information concerning a type of fault that has occurred in the device and identification information assigned to each of the plurality of devices are associated with each other,
wherein the acquisition unit acquires the fault information of the device in which the fault has occurred, and
wherein the display control unit performs control to cause the display unit to display the plurality of groups in such a manner that, on the basis of the fault occurrence information accumulated by the accumulation unit, a device in which the same type of fault as a type of fault indicated by the fault information acquired by the acquisition unit has occurred is recognizable.

13. The fault diagnosis apparatus according to claim 9, wherein the installation environment information for each of the plurality of devices includes a plurality of items about at least one of information concerning hardware of a connected device to which the device is connected, information concerning software used in the device, or information concerning maintenance of the device.

14. The fault diagnosis apparatus according to claim 1, further comprising:
an accumulation unit that accumulates fault occurrence information in which fault information concerning a type of fault that has occurred in the device in which the fault has occurred and identification information assigned to each of the plurality of devices are associated with each other,
wherein the acquisition unit acquires the fault information of the device in which the fault has occurred, and wherein the display control unit performs control to cause the display unit to display the plurality of groups in such a manner that, on the basis of the fault occurrence information accumulated by the accumulation unit, a device in which the same type of fault as a type of fault indicated by the fault information acquired by the acquisition unit has occurred is recognizable.

15. The fault diagnosis apparatus according to claim 1, wherein the installation environment information for each of the plurality of devices includes a plurality of items about at least one of information concerning hardware of a connected device to which the device is connected, information concerning software used in the device, or information concerning maintenance of the device.

16. The fault diagnosis apparatus according to claim 1, wherein the extraction unit extracts items in the installation environment information, each item representing one of a plurality of features as the different feature in descending order from a feature having a highest degree of difference.

17. The fault diagnosis apparatus according to claim 1, further comprising:
an acceptance unit that accepts an input of the installation environment information of the device in which the fault has occurred,
wherein the classification unit classifies, on the basis of the installation environment information accepted by the acceptance unit, the device in which the fault has occurred in any one of a plurality of groups classified on the basis of the installation environment information acquired by the acquisition unit.

18. The fault diagnosis apparatus according to claim 1, wherein the device is a medical device.

19. A non-transitory computer readable recording medium storing a fault diagnosis program for causing a computer to function as an acquisition unit, a classification unit, an extraction unit, and a display control unit of the fault diagnosis apparatus according to claim 1.

20. A fault diagnosis method comprising:
acquiring, for each of a plurality of devices, installation environment information including a plurality of items about an installation environment in which each of the plurality of devices is installed;
classifying the plurality of devices into a plurality of groups on the basis of the installation environment information;
extracting an item in the installation environment information representing a feature of a group to which a device in which a fault has occurred among the plurality of devices belongs, the feature being different from a feature of other groups; and
performing control to cause a display unit to display an extraction result.

* * * * *